United States Patent
Mou et al.

(10) Patent No.: US 10,921,221 B2
(45) Date of Patent: Feb. 16, 2021

(54) GAS DETECTING DEVICE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 192 days.

(21) Appl. No.: 16/243,398

(22) Filed: Jan. 9, 2019

(65) Prior Publication Data

US 2019/0234838 A1 Aug. 1, 2019

(30) Foreign Application Priority Data

Jan. 31, 2018 (TW) .............................. 107103540 A (51) Int. Cl.
*G01N 1/22* (2006.01)
*G01N 33/00* (2006.01)

(52) U.S. Cl.
CPC ......... *G01N 1/2273* (2013.01); *G01N 33/004* (2013.01); *G01N 33/0009* (2013.01); *G01N 33/0022* (2013.01); *G01N 33/0047* (2013.01)

(58) Field of Classification Search
CPC ............. G01N 1/2273; G01N 33/0009; G01N 33/0022
See application file for complete search history.

(56) References Cited

U.S. PATENT DOCUMENTS

2010/0229658 A1   9/2010   Glezer et al.
2012/0143515 A1*  6/2012   Norman .............. G01N 33/0031
                                                         702/24
(Continued)

FOREIGN PATENT DOCUMENTS

CN          106233119 A      12/2016
JP          2003-98139 A      4/2003
(Continued)

OTHER PUBLICATIONS

Extended European Search Report, dated Jul. 24, 2019, for European Application No. 19150966.0.

*Primary Examiner* — Paul M. West
(74) *Attorney, Agent, or Firm* — Birch, Stewart, Kolasch & Birch, LLP (57) ABSTRACT

A gas detecting device includes a casing, at least one gas transporting actuator, at least one valve and at least one external sensor. The easing has an airflow chamber, an inlet, a branch channel and a connection channel. The airflow chamber communicates with an environment outside the casing through the inlet, and the branch channel communicates with the airflow chamber and the connection channel. The gas transporting actuator is disposed within the branch channel for transporting air into the airflow chamber and the branch channel from the inlet, and has a nozzle plate, a chamber frame, an actuator, an insulation frame and a conducting frame. The valve is disposed between the connection channel and the branch channel for controlling the air to flow into the connection channel. The external sensor is detachably disposed within the connection channel and has a sensor for measuring the air in the connection channel.

14 Claims, 10 Drawing Sheets

(56) References Cited

U.S. PATENT DOCUMENTS

| | | | |
|---|---|---|---|
| 2014/0261348 A1* | 9/2014 | Wahl | F02D 41/146 |
| | | | 123/672 |
| 2014/0377099 A1 | 12/2014 | Hsueh et al. | |
| 2016/0223437 A1 | 8/2016 | Ajay et al. | |
| 2016/0245714 A1 | 8/2016 | Gagne et al. | |
| 2016/0327416 A1 | 11/2016 | Gagne et al. | |

FOREIGN PATENT DOCUMENTS

| | | |
|---|---|---|
| TW | 201530112 A | 8/2015 |
| TW | M553417 U | 12/2017 |

* cited by examiner

GAS DETECTING DEVICE

FIELD OF THE DISCLOSURE

The present disclosure relates to a gas detecting device, and more particularly to a gas detecting device having a gas transporting actuator for gas transportation.

BACKGROUND OF THE DISCLOSURE

Nowadays, the air pollution problems are becoming increasingly serious in our country and its neighboring regions. There are many harmful gases to human body in daily life. If it fails to be detected in time, it will affect the health of the human body.

Moreover, there are different demands of gas detection for users in different places (e.g., factories, offices or homes). For example, gas sensors for detecting volatile gases or toxic gases causing inhalation injuries are suitably used in factories. Carbon monoxide sensors, carbon dioxide sensors, temperature sensors or humidity sensors are suitably used in homes and offices. Since the commercially available gas detecting device is an integral gas detecting device, some drawbacks occur. For example, the type of the gas to be detected has been determined before the gas detecting device leaves the factory and cannot be changed by the users according to the particle requirements. In that, a gas detecting device cannot provide complete detections to meet the requirements of users. Therefore, there is a need of providing a gas detecting device capable of performing gas detection according to different requirements to address the above-mentioned issues.

SUMMARY OF THE DISCLOSURE

An object of the present disclosure is to provide a gas detecting device having an external sensor for detecting air and providing users with air information timely and accurately. The external sensor of the gas detecting device can be selected and matched according to the requirements of the users. It has benefits for achieving the purposes of easy replacement and improving practicality and convenience.

In accordance with an aspect of the present disclosure, a gas detecting device is provided. The gas detecting device includes a casing, at least one gas transporting actuator, at least one valve and at least one external sensor. The casing has an airflow chamber, at least one inlet, at least one branch channel and at least one connection channel. The airflow chamber is in fluid communication with an environment outside the casing through the at least one inlet, the at least one branch channel is in fluid communication with the at least one airflow chamber, and the at least one connection channel is in fluid communication with the at least one branch channel. The at least one gas transporting actuator is disposed on the at least one branch channel, has a nozzle plate, a chamber frame, an actuator, an insulation frame and a conducting frame, and is actuated to inhale air into the at least one airflow chamber through the at least one inlet and transport the air into the at least one branch channel. The at least one valve is disposed between the at least one connection channel and the at least one branch channel to control the air to flow into the at least one connection channel. The at least one external sensor is detachably assembled in the at least one connection channel and includes a sensor to measure the air in the at least one connection channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1 to 4. The present disclosure provides a gas detecting device 100 including at least one casing 1, at least one gas transporting actuator 2, at least one valve 3, at least one external sensor 4, at least one airflow chamber 11, at least one inlet 12, at least one branch channel 13, at least one connection channel 14, at least one nozzle plate 21, at least one chamber frame 22, at least one actuator 23, at least one insulation frame 24, at least one conducting frame 25 and at least one external sensor 4. The numbers of the casing 1, the airflow chamber 11, the nozzle plate 21, the chamber frame 22, the actuator 23, the insulation frame 24, the conducting frame 25 and the external sensor 4 are exemplified by one for each respectively in the following embodiments but not limited thereto. It is noted that each of the casing 1, the airflow chamber 11, the nozzle plate 21, the chamber frame 22, the actuator 23, the insulation frame 24, the conducting frame 25 and the external sensor 4 can also be provided in plural numbers.

Figure 1:
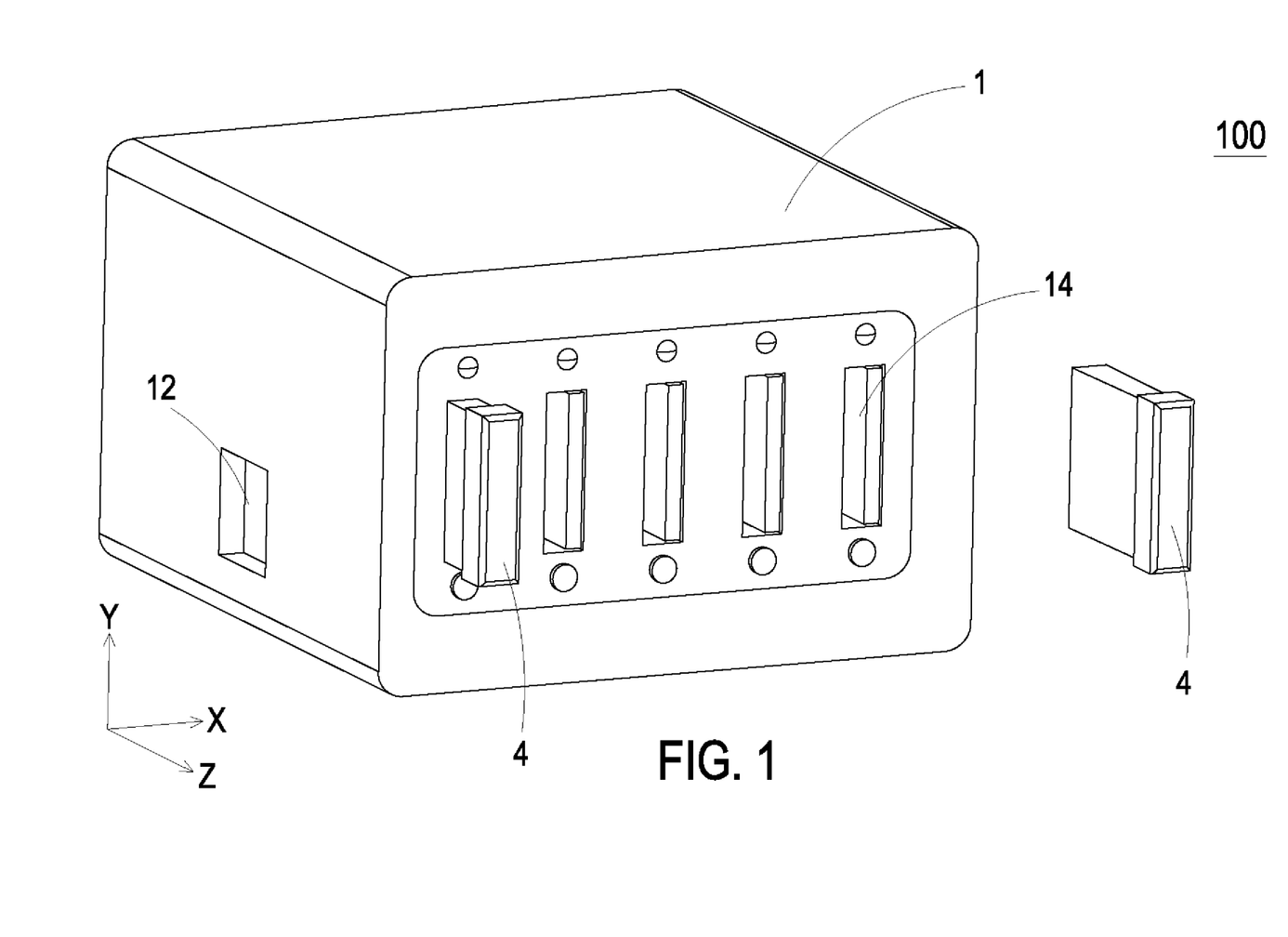
FIG. 1 is a schematic perspective view illustrating a gas detecting device according to an embodiment of the present disclosure.
Figure 2:
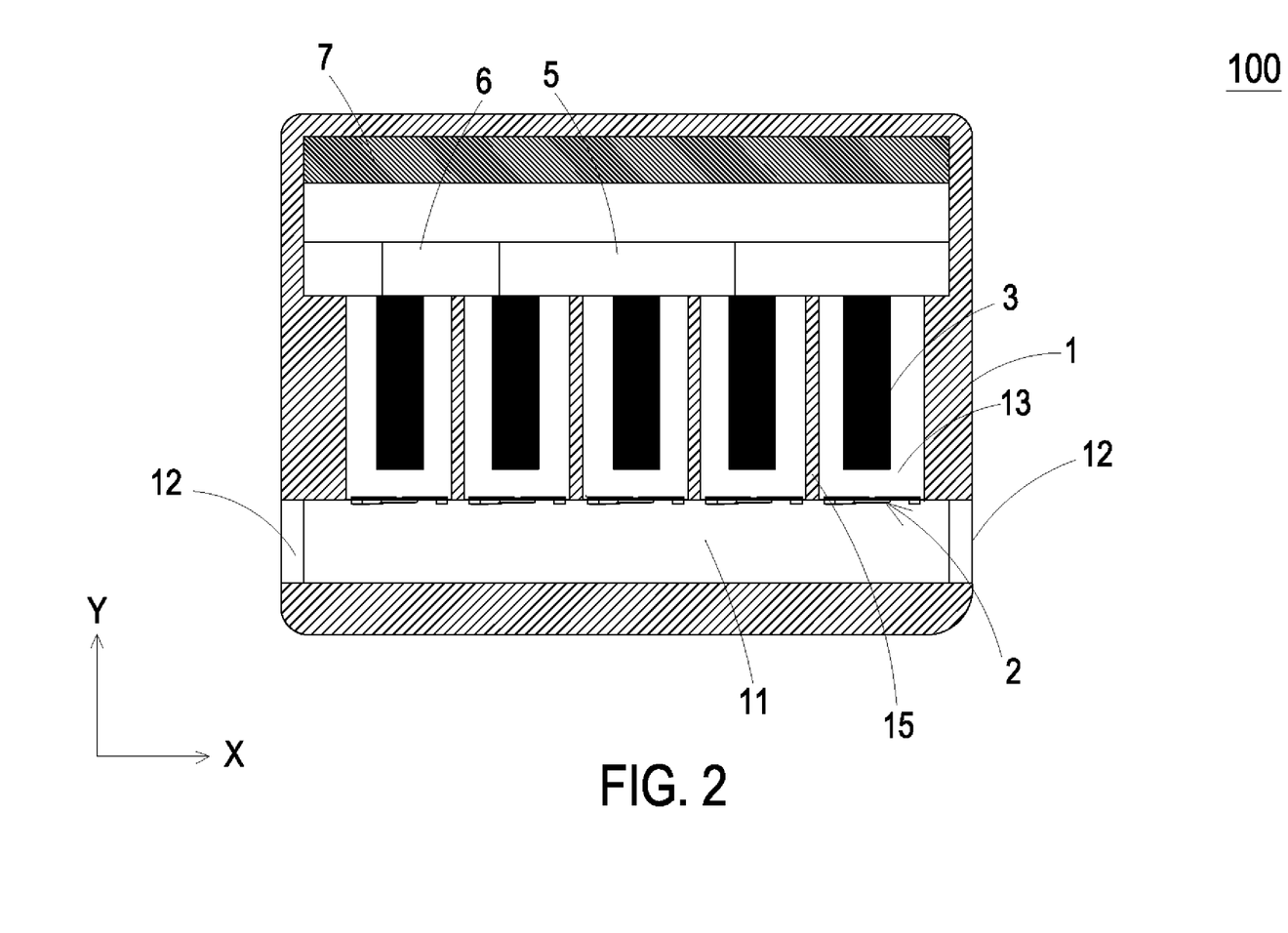
FIG. 2 is a schematic cross-sectional view illustrating the gas detecting device of FIG. 1.
Figure 3:
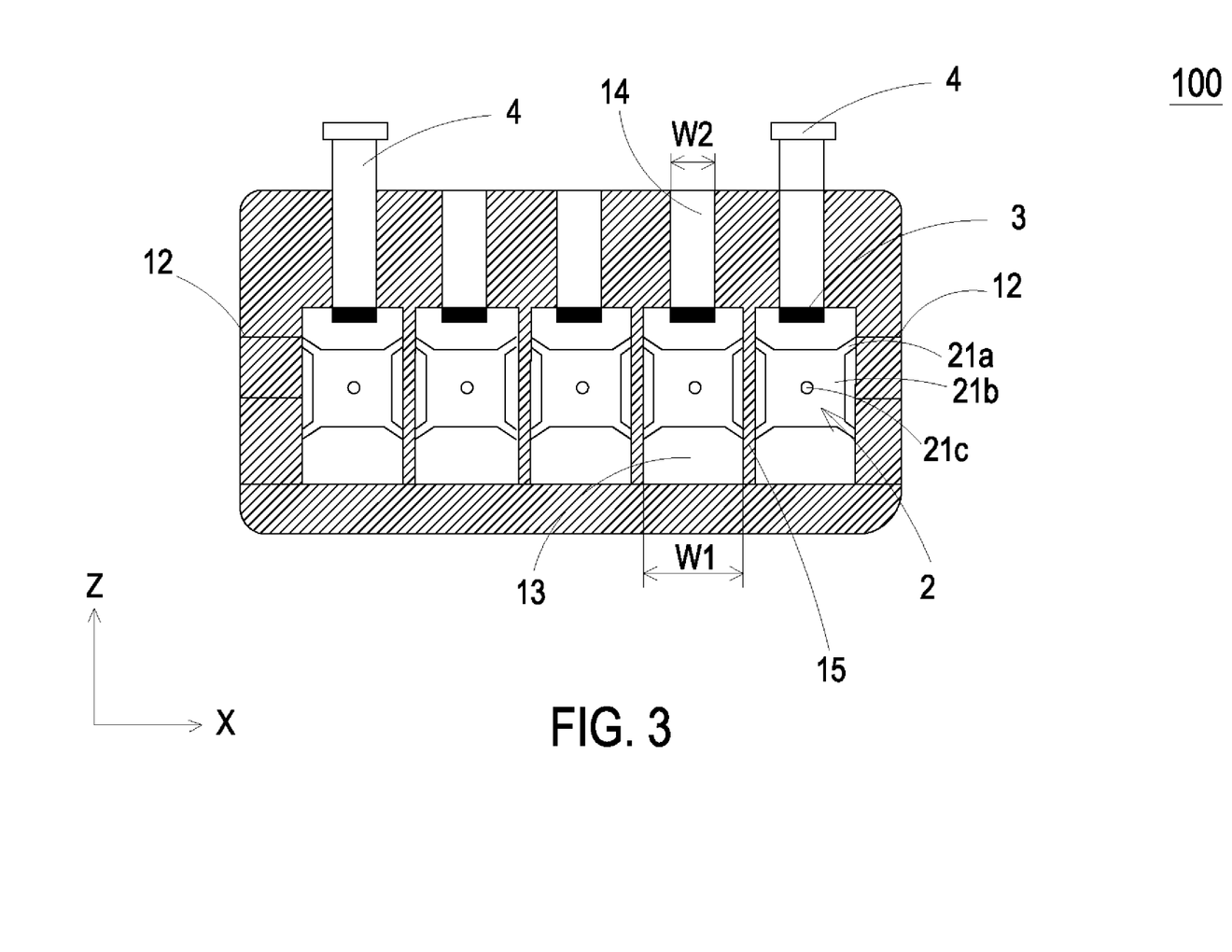
FIG. 3 is a schematic cross-sectional view illustrating a gas transporting actuator of a gas detecting device of the present disclosure.

The present disclosure provides a gas detecting device 100. Please refer to FIGS. 1 to 3. FIG. 1 is a three-dimensional view of the present disclosure. FIG. 2 is a sectional view taken in the X-Y plane, and FIG. 3 is a sectional view taken in the X-Z plane. In the embodiment, the gas detecting device 100 includes a casing 1, at least one gas transporting actuator 2, at least one valve 3 and at least one external sensor 4. The casing 1 has an airflow chamber 11, at least one inlet 12, at least one branch channel 13 and at least one connection channel 14. The numbers of the branch channels 13, the connection channels 14, the gas transporting actuators 2 and the valves 3 are corresponding to each other, respectively. The numbers of the branch channels 13, the connection channels 14, the gas transporting actuators 2 and the valves 3 are exemplified by five for each respectively in the following embodiments but not limited thereto. The airflow chamber 11 is in fluid communication with the environment outside the casing 1 through the at least one inlet 12 and is in fluid communication with the five branch channels 13. The casing 1 includes a plurality of partition plates 15 used to space apart the five branch channels 13 and the five connection channels 14. More specifically, the casing 1 has a convergence chamber disposed on the airflow chamber 11 along the Y-axis and extending beyond the airflow chamber 11 along the Z-axis. The partition plates 15 divides the convergence chamber into the five branch channels 13, and thus defines five parts, each of which consists of the branch channel 13 and the connection channel 14, separated from each other. The airflow chamber 11 extends along the X-axis and is exposed to the environment on both ends via the at least one inlet 12, and also connects to the five branch channels 13 along the Y-axis. The five connection channels 14 extend along the Z-axis to a side surface of the casing 1, and are open to the environment outside the casing 1. Moreover, the branch channel 13 has a width W1 and the connection channel 14 has a width W2 along the X-axis. The width W1 is greater than the width W2. The five connection channels 14 are corresponding in number and positions to and in fluid communication with the five branch channels 13. The five gas transporting actuators 2 are correspondingly disposed in the five branch channels 13, respectively, to transport air contained in the airflow chamber 11 into the corresponding branch channels 13. The five valves 3 are correspondingly disposed between the five connection channels 14 and the five branch channels 13 to control the air to flow into the corresponding connection channels 14. That is, the valve 3 extends along a direction substantially perpendicular to the gas transporting actuator 2 and seals the junction between the connection channel 14 and the branch channel 13. Moreover, the five external sensors 4 are detachably assembled in the five corresponding connection channels 14, respectively. Each external sensor 4 includes a sensor (not shown) disposed therein. In the embodiment, the sensor of the external sensor 4 can be at least one selected from the group consisting of an oxygen sensor, a carbon monoxide sensor, a carbon dioxide sensor and combinations thereof. In an embodiment, the sensor of the external sensor 4 can be a volatile organic compound sensor. Alternatively, the sensor of the external sensor 4 can be at least one selected from the group consisting of a bacterial sensor, a virus sensor, a microorganism sensor and combinations thereof. Alternatively, the sensor of the external sensor 4 can be at least one selected form the group consisting of a temperature sensor, a humidity sensor and combinations thereof. In that, the sensor of the external sensor 4 is used to measure the air contained in the connection channel 14.

Figure 4:
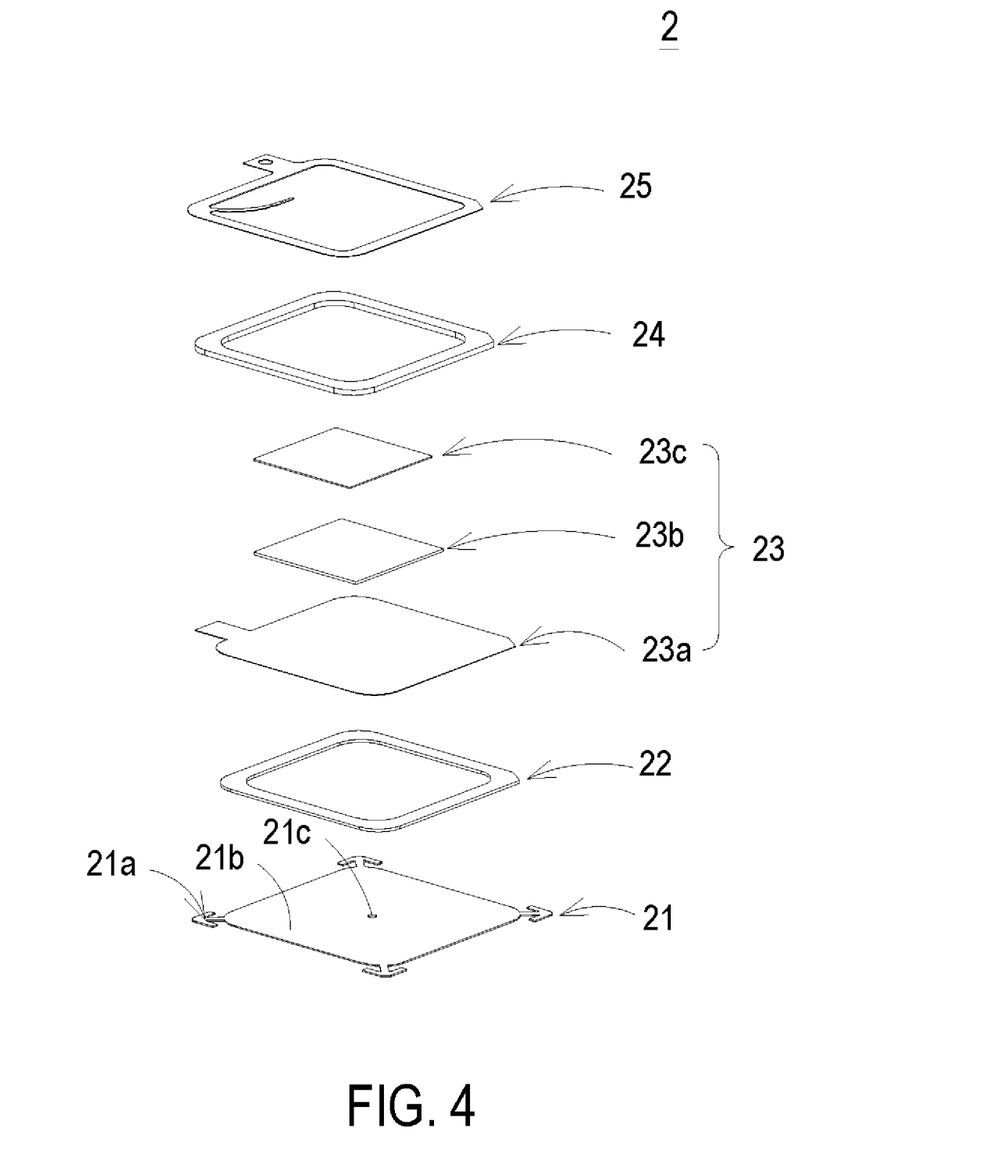
FIG. 4 is an exploded view illustrating the gas transporting actuator of the present disclosure.
Figure 5A:
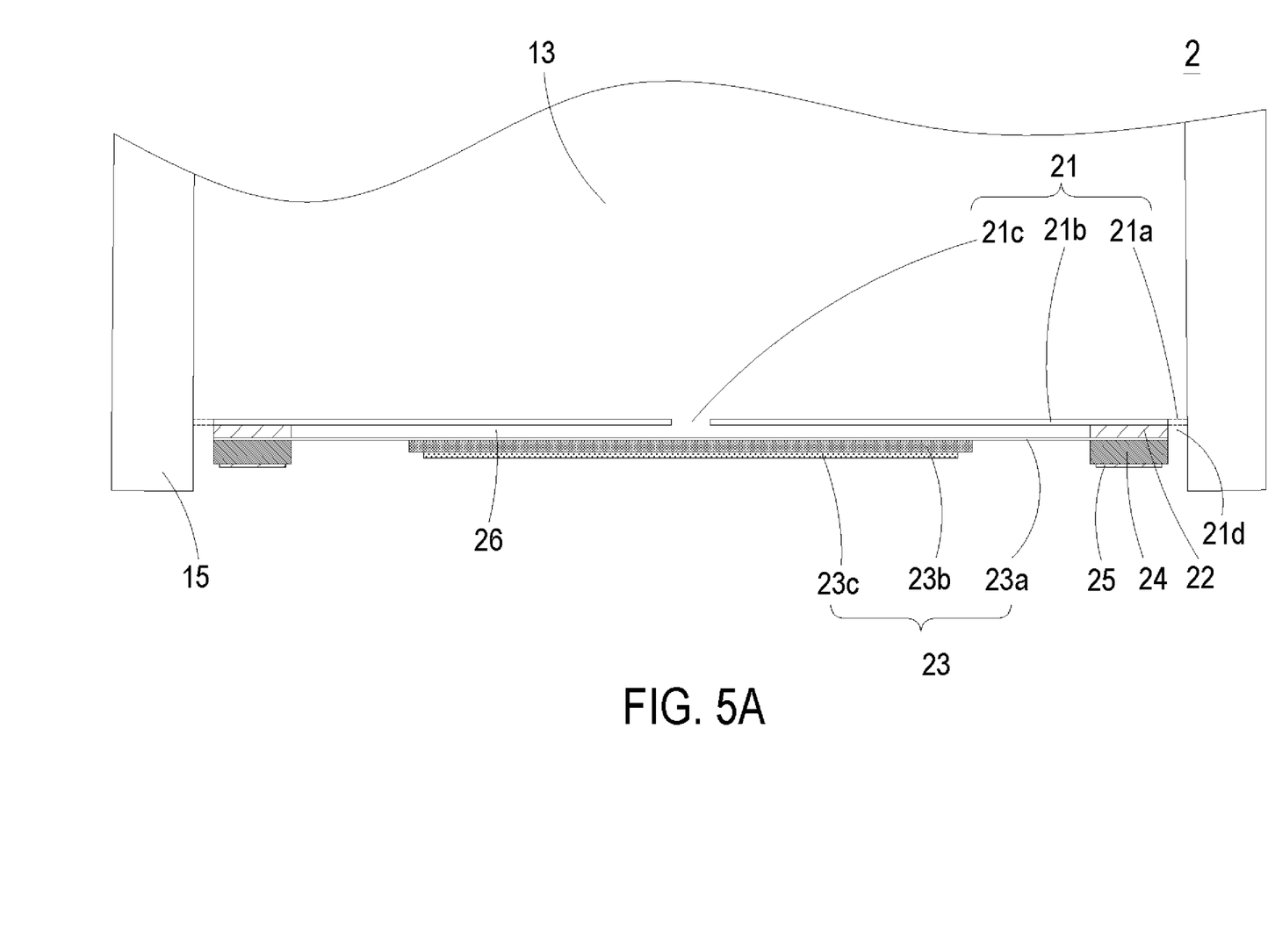
FIG. 5A is a schematic cross-sectional view illustrating the gas transporting actuator of FIG. 4.
Figure 5B:
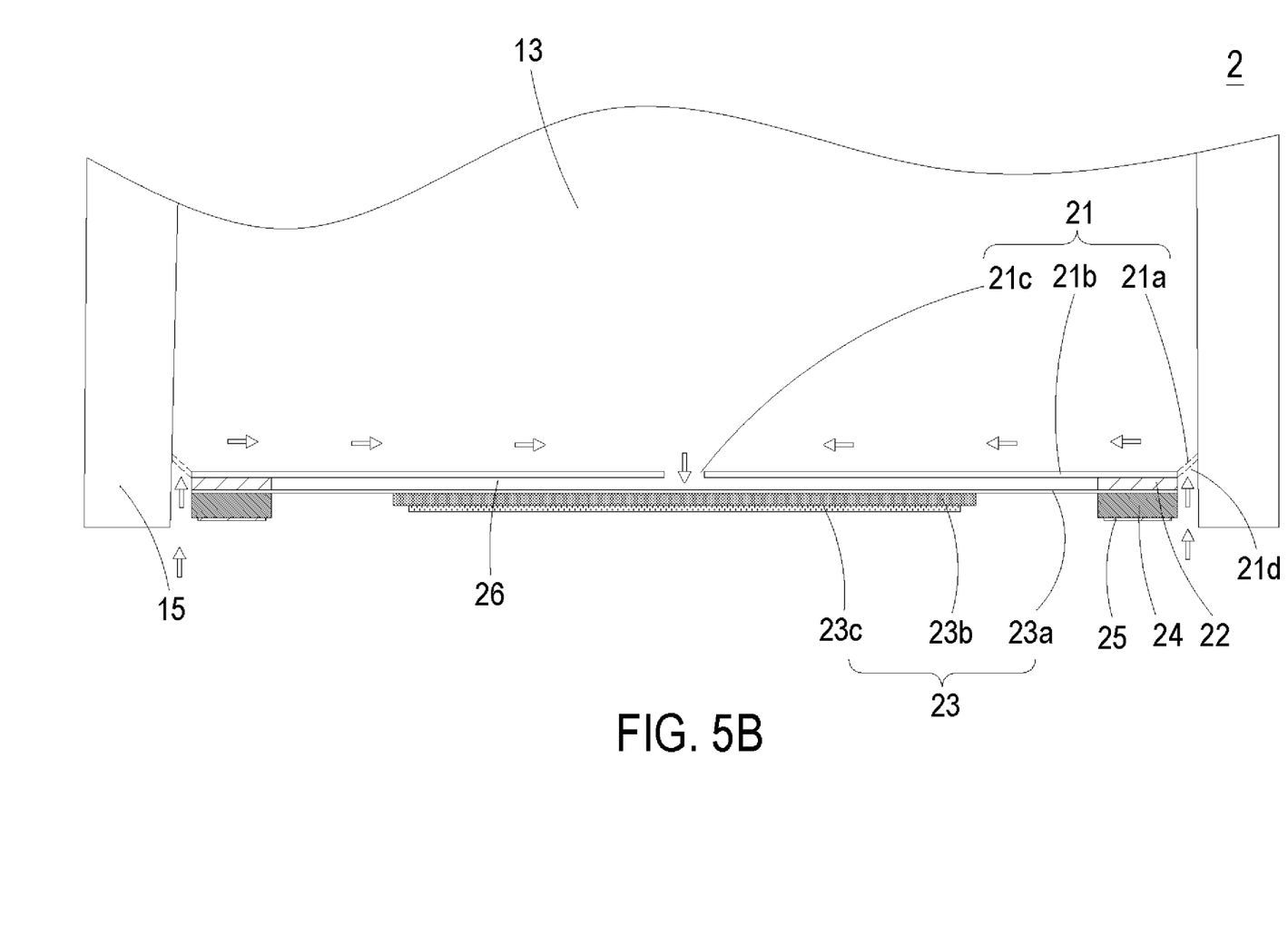
FIG. 5B and FIG. 5C are schematic views illustrating actions of the gas transporting actuator of FIG. 5A.
Figure 5C:
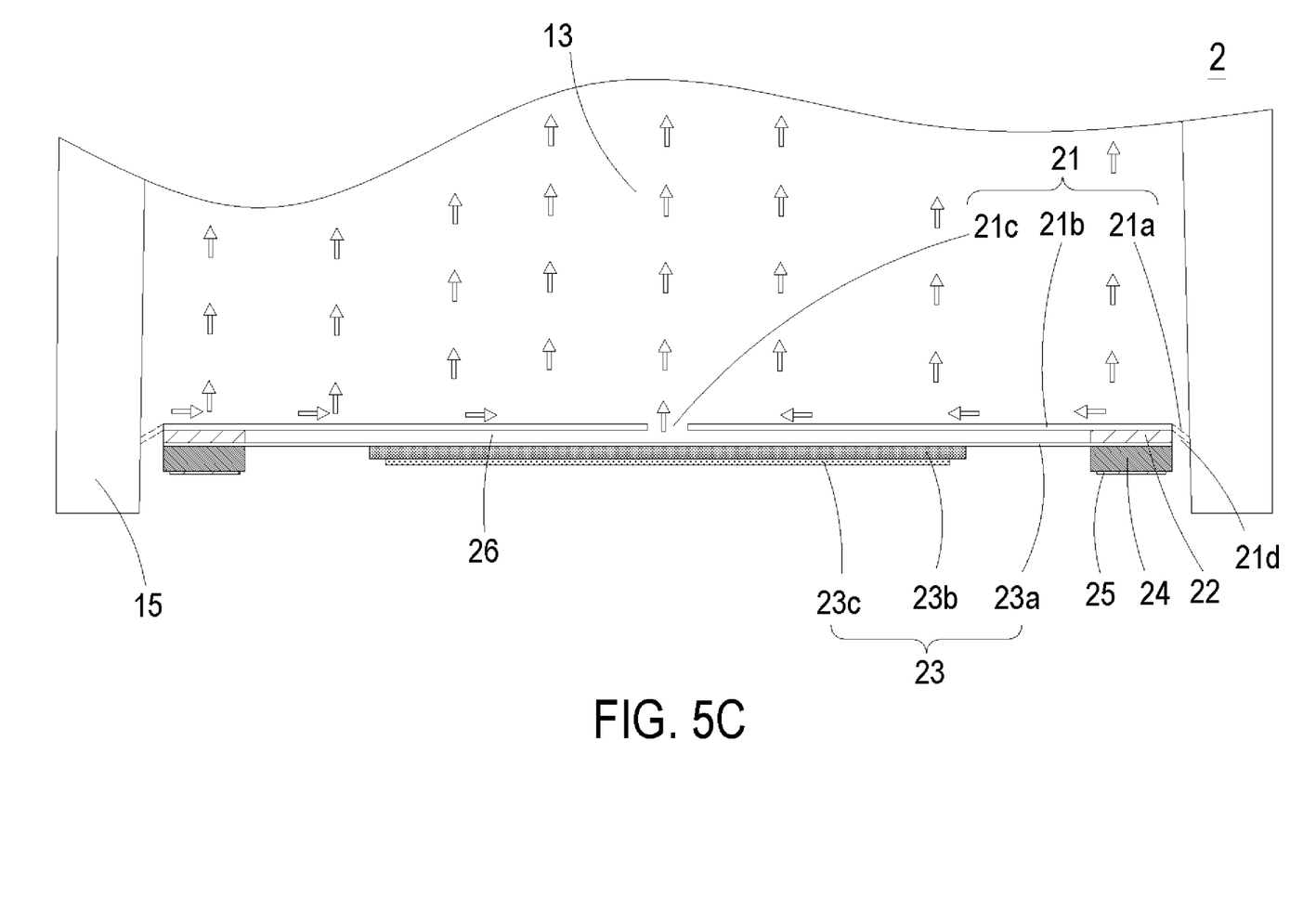

Please refer to FIGS. 3, 4 and 5A to 5C. FIG. 4 is an exploded view illustrating the gas transporting actuator of the present disclosure. FIG. 5A is a schematic cross-sectional view illustrating the gas transporting actuator of FIG. 4. FIG. 5B and FIG. 5C are schematic views illustrating actions of the gas transporting actuator of FIG. 5A. In the embodiment, the gas transporting actuator 2 includes a nozzle plate 21, a chamber frame 22, an actuator 23, an insulation frame 24 and a conducting frame 25 stacked on each other sequentially. Except for the nozzle plate 21, the rest components of the gas transporting actuator 2 are omitted for ease of understanding, as shown in FIG. 3. The nozzle plate 21 includes a plurality of brackets 21a, a suspension plate 21b, a central aperture 21c and at least one vacant space 21d. The suspension plate 21b is permitted to undergo a bending vibration. The plurality of brackets 21a are connected to the periphery of the suspension plate 21b. In the embodiment, there are four brackets 21a, which are connected to four corners of the suspension plate 21b, respectively, but the present disclosure is not limited thereto. The suspension plate 21b is sleeved and fixed on the partition plate 15 through the plurality of brackets 21a. Consequently, the nozzle plate 21 is positioned and accommodated within the corresponding branch channel 13. In this way, the gas transporting actuator 2 is placed at the junction between the airflow chamber 11 and the branch channel 13. In some embodiments, the gas transporting actuator 2 may be placed deep inside the branch channel 13 as required. The central aperture 21c is formed at the center of the suspension plate 21b, and the vacant spaces 21d are airflow apertures formed among the plurality of brackets 21a, the suspension plate 21b and the partition plate 15. It is noted that the plurality of brackets 21a connect to the partition plate 15 along the X-Z plane, and thereby the central aperture 21c may not face the valve 3 and the connection channel 14. The chamber frame 22 is carried and stacked on the suspension plate 21b. The actuator 23 is carried and stacked on the chamber frame 22 and includes a piezoelectric carrying plate 23a, an adjusting resonance plate 23b and a piezoelectric plate 23c. The piezoelectric carrying plate 23a is carried and stacked on the chamber frame 22. The adjusting resonance plate 23b is carried and stacked on the piezoelectric carrying plate 23a. The piezoelectric plate 23c is carried and stacked on the adjusting resonance plate 23b. As the piezoelectric plate 23c is actuated by an applied voltage, the piezoelectric plate 23c deforms to drive the piezoelectric carrying plate 23a and the adjusting resonance plate 23b to bend and vibrate in the reciprocating manner. The insulation frame 24 is carried and stacked on the piezoelectric carrying plate 23a of the actuator 23. The conducting frame 25 is carried and stacked on the insulation frame 24, A resonance chamber 26 is defined by the actuator 23, the chamber frame 22 and the suspension plate 21b collaboratively. The adjusting resonance plate 23b is thicker than the piezoelectric carrying plate 23a.

Please refer to FIG. 5B. When the piezoelectric plate 23c of the actuator 23 is actuated by an applied voltage, the piezoelectric plate 23c of the actuator 23 is deformed by the piezoelectric effect, and the adjusting resonance plate 23b and the piezoelectric carrying plate 23a are simultaneously driven to vibrate. Thereby, the nozzle plate 21 is driven to move due to the Helmholtz resonance effect, and the actuator 23 is displaced downwardly. Since the actuator 23 is displaced downwardly, the volume of the branch channel 13 is expended and the air contained in the airflow chamber 11 is transported into the branch channel 13 through the vacant spaces 21d formed among the plurality of brackets 21a of the nozzle plate 21 due to the pressure gradient, and further transported into the resonance chamber 26 through the central aperture 21c. As shown in FIG. 5C, the air flows into the branch channel 13 continuously. At the meantime, the actuator 23 is driven to vibrate upwardly in response to the applied voltage, and the volume of the branch channel 13 is shrunken. The air is compressed to flow into the connection channel 14, and the air contained in the resonance chamber 26 is ejected out through the central aperture 21c. Consequently, the air is provided to the sensor of the external sensor 4 for detecting. By the gas transporting actuator 2, the air is inhaled from the environment outside the casing 1 through the inlet 12, and the air contained in the airflow chamber 11 can be further transported into the branch channel 13 and the connection channel 14 continuously. Thus, the air contained in the connection channel 14 is provided to the external sensor 4 to detect a specific gas compound.

Figure 6:
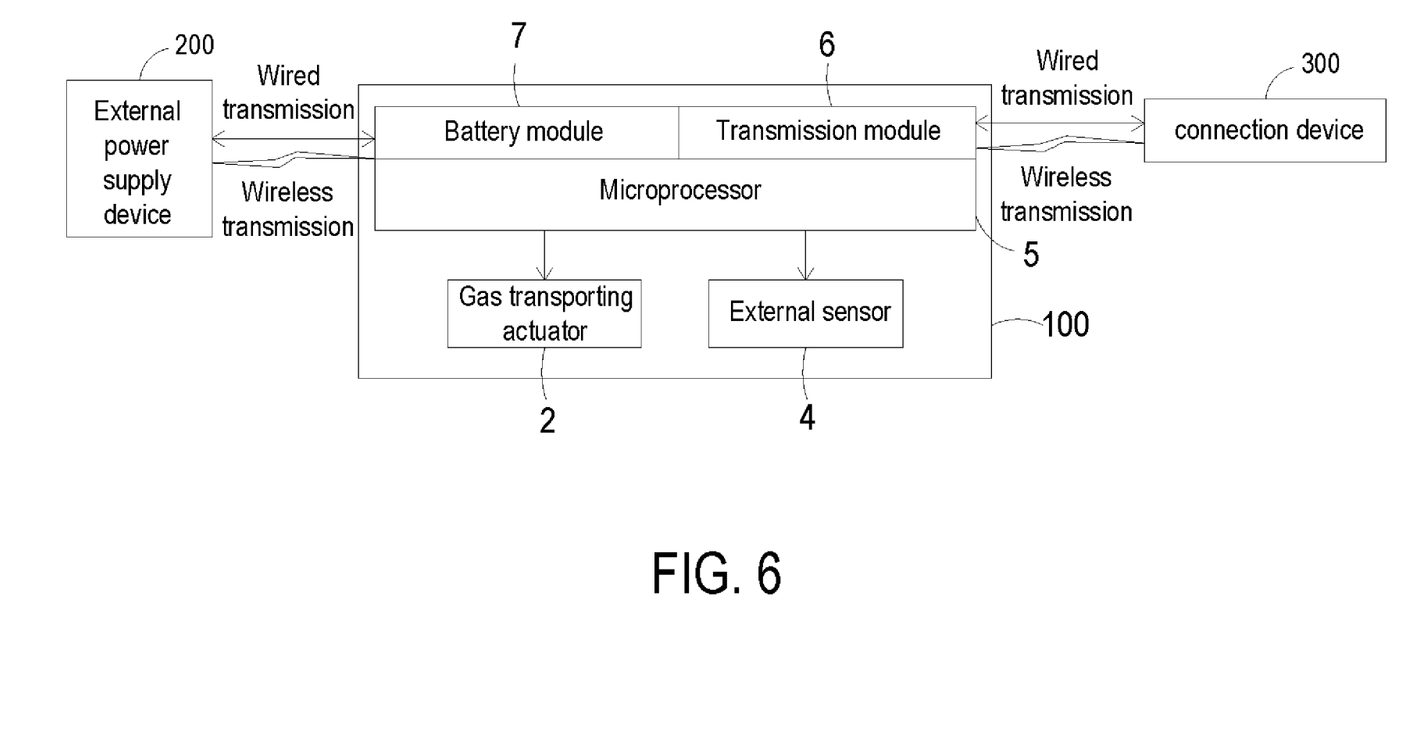
FIG. 6 is a block diagram of the gas detecting device of the present disclosure.

Please refer to FIGS. 2 and 6. The gas detecting device 100 further includes a microprocessor 5, a transmission module 6 and a battery module 7. The microprocessor 5 is electrically connected to the battery module 7, the transmission module 6, the gas transporting actuator 2 and the valve 3 to control the actuation of the gas transporting actuator 2. The external sensor 4 is assembled in the connection channel 14, and is electrically connected to and in data communication with the microprocessor 5. Therefore, detected results from the sensor of the external sensor 4 can be analyzed, calculated, stored and converted into detected values by the microprocessor 5. When the microprocessor 5 actuates the gas transporting actuator 2, the gas transporting actuator 2 starts to inhale the air and transport the air into the branch channel 13 and the connection channel 14. In that, the sensor of the external sensor 4 disposed in the connection channel 14 starts to measure the air contained in the connection channel 14 and transmit the detected results to the microprocessor 5. The detected results are analyzed and converted into the detected values by the microprocessor 5 and the detected values are stored in the microprocessor 5. The detected values stored in the microprocessor 5 are transmitted to a connection device 300 via the transmission module 6, so that information carried by the detected values are displayed, stored and transmitted through the connection device 300, and a notification alert is issued. The connection device 300 can be at least one selected from the group consisting of a cloud system, a portable device, a computer system, a display device and combinations thereof.

In addition, the transmission module 6 can be at least one selected from the group consisting of a wired transmission module and a wireless transmission module, so as to achieve the transmission with the connection device 300. In an embodiment, the transmission module 6 can be the wired transmission module and selected from the group consisting of a USB transmission module, a mini-USB transmission module, a micro-USB transmission module and combinations thereof. In another embodiment, the transmission module 6 can be the wireless transmission module and selected from the group consisting of a Wi-Fi transmission module, a Bluetooth transmission module, a radio frequency identification transmission module, a near field communication transmission module and combinations thereof.

As mentioned above, the battery module 7 is used to store electrical energy and output the electrical energy, so that the electrical energy is provided to the microprocessor 5 to control the gas transporting actuator 2, the transmission module 6, the valve 3 and the sensor of the external sensor 4 to be actuated. Moreover, the battery module 7 is electrically connected to an external power supply device 200 to receive electrical energy for storage. The external power supply device 200 can transmit the electrical energy to the battery module 7 by means of a wired transmission technology or transmit the electrical energy to the battery module 7 by a wireless transmission technology, but not limited thereto.

Figure 7A:
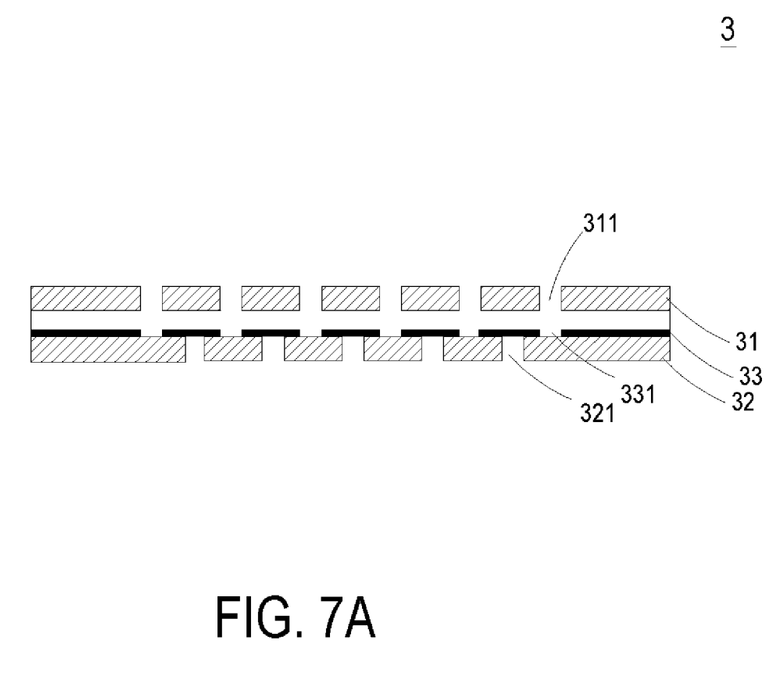
FIGS. 7A and 7B are schematic cross-sectional views illustrating the actions of the valve used in the gas detecting device according to an embodiment of the present disclosure.

Please refer to FIGS. 2 and 7A. In the embodiment, the valve 3 includes a stationary component 31, a sealing component 32 and a displacement component 33. The displacement component 33 is disposed between the stationary component 31 and the sealing component 32. The stationary component 31 has a plurality of first orifices 311.

The displacement component 33 has a plurality of second orifices 331 respectively corresponding in position to the plurality of first orifices 311 of the stationary component 31. That is, the plurality of first orifices 311 of the stationary component 31 are aligned with the plurality of second orifices 331 of the displacement component 33. The sealing component 32 has a plurality of third orifices 321. The plurality of third orifices 321 of the sealing component 32 are misaligned with the plurality of first orifices 311 of the stationary component 31.

Please refer to FIGS. 7A and 6. In a first aspect of the valve 3 in the present disclosure, the displacement component 33 is made of a charged material, and the stationary component 31 is made of a bipolar conductive material. In case that the displacement component 33 and the stationary component 31 are controlled by the microprocessor 5 to maintain in the same polarity, the displacement component 33 moves toward the sealing component 32 so that the valve 3 is in a closed state. Please refer to FIG. 7B. The displacement component 33 is made of a charged material, and the stationary component 31 is made of a bipolar conductive material. In case that the displacement component 33 and the stationary component 31 are controlled by the microprocessor 5 to maintain in opposite polarity, the displacement component 33 moves toward the stationary component 31 so that the valve 3 is in an open state. According to the above descriptions, it is understood that by adjusting the polarity of the stationary component 31, the displacement member 33 is moved to switch the valve 3 between the open state and the closed state. Since the microprocessor 5 is electrically connected to the valve 3, the polarity of the stationary component 31 can be controlled by the microprocessor 5.

Figure 7B:
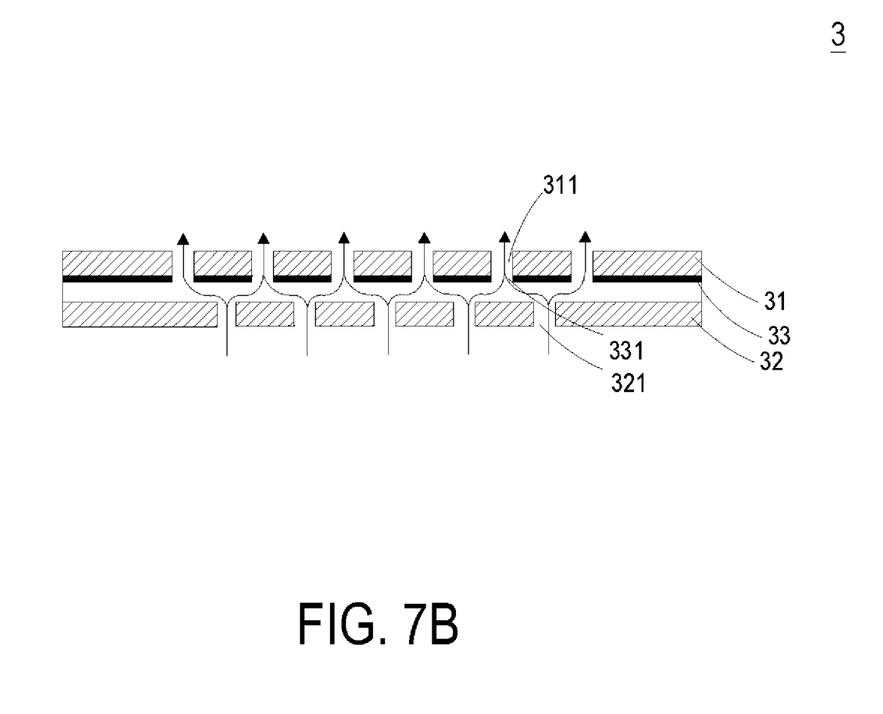

In a second aspect of the valve 3 in the present disclosure, the displacement component 33 is made of a magnetic material, and the stationary component 31 is made of an electromagnet material and can be controlled to change its magnetic polarity. When the displacement component 33 and the stationary component 31 are controlled by the microprocessor 5 to maintain in the same polarity, the displacement component 33 moves toward the sealing component 32 so that the valve 3 is in the closed state. Alternatively, when the displacement component 33 and the stationary component 31 are controlled by the microprocessor 5 to maintain in opposite polarity, the displacement component 33 moves toward the stationary component 31 so that the valve 3 is in the open state. According to the above descriptions, it is understood that by adjusting the polarity of the stationary component 31, the displacement member 33 is moved to switch the valve 3 between the open state and the closed state. The polarity of the stationary component 31 can be controlled by the microprocessor 5.

In summary, the present disclosure provides a gas detecting device. By separately setting a plurality of gas transporting actuators in the different branch channels of the gas detecting device, the air contained in the airflow chamber is transported into the branch channel and the connection channel, so that the external sensor in the connection channel can detect the air flowing into the connection channel and obtain the air quality information. The external sensor is detachably assembled in the connection channel, so that the user can easily replace the required sensor according to the particle requirements.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device comprising:
   a casing having an airflow chamber, at least one inlet, at least one branch channel, at least one connection channel and at least one partition plate, wherein the airflow chamber is in fluid communication with an environment outside the casing through the at least one inlet, the at least one branch channel is in fluid communication with the airflow chamber, and the at least one connection channel is in fluid communication with the at least one branch channel;
   at least one gas transporting actuator disposed on the at least one branch channel and having a nozzle plate, a chamber frame, an actuator, an insulation frame and a conducting frame, wherein the gas transporting actuator is actuated to inhale air into the at least one airflow chamber through the at least one inlet and transport the air into the at least one branch channel, wherein the at least one partition plate is used to space apart the at least one branch channel and the at least one connection channel, and the nozzle plate of the at least one gas transporting actuator is fixed on the at least one partition plate, so that the nozzle plate is positioned and accommodated within the at least one branch channel;
   at least one valve disposed between the at least one connection channel and the at least one branch channel to control the air to flow into the at least one connection channel; and
   at least one external sensor detachably assembled in the at least one connection channel and comprising a sensor to measure the air in the at least one connection channel.

2. The gas detecting device according to claim 1, wherein the nozzle plate has a plurality of brackets, a suspension plate and a central aperture, wherein the suspension plate is permitted to undergo a bending vibration, the plurality of brackets are sleeved and fixed on the at least one partition plate to position the nozzle plate within the at least one branch channel, and at least one vacant space is defined by the plurality of brackets, the suspension plate and the partition plate, wherein the chamber frame is carried and stacked on the suspension plate, the actuator is carried and stacked on the chamber frame and is configured to bend and vibrate in a reciprocating manner by an applied voltage, the insulation frame is carried and stacked on the actuator, and the conducting frame is carried and stacked on the insulation frame, wherein a resonance chamber is defined by the actuator, the chamber frame and the suspension plate collaboratively, wherein by driving the actuator to drive the nozzle plate to generate a resonance, the suspension plate of the nozzle plate vibrates and displaces in a reciprocating manner, so as to make the air flow through the at least one vacant space into the branch channel and achieve air transportation at high speed.

3. The gas detecting device according to claim 2, wherein the actuator comprises:
   a piezoelectric carrying plate carried and stacked on the chamber frame;
   an adjusting resonance plate carried and stacked on the piezoelectric carrying plate; and
   a piezoelectric plate carried and stacked on the adjusting resonance plate, wherein the piezoelectric plate is configured to drive the piezoelectric carrying plate and the adjusting resonance plate to bend and vibrate in the reciprocating manner by the applied voltage.

4. The gas detecting device according to claim 1, further comprising a microprocessor and a transmission module, wherein the microprocessor is used to control the transmission module, the gas transporting actuator and the valve to be actuated, and the sensor of the external sensor assembled in the connection channel is electrically connected to and in data communication with the microprocessor, wherein detected results from the sensor are analyzed and converted into detected values by the microprocessor, and the transmission module transmits the detected values to a connection device so that information carried by the detected values are displayed, stored and transmitted through the connection device and a notification alert is issued.

5. The gas detecting device according to claim 4, wherein the connection device is at least one selected from the group consisting of a cloud system, a portable device, a computer system and combinations thereof.

6. The gas detecting device according to claim 4, wherein the valve comprises a stationary component, a sealing component and a displacement component, wherein the displacement component is disposed between the stationary component and the sealing component, the stationary component has a plurality of first orifices, the displacement component has a plurality of second orifices, and the sealing component has a plurality of third orifices, wherein the plurality of the first orifices of the stationary component are aligned with the plurality of the second orifices of the displacement component, and the plurality of the third orifices of the sealing component are misaligned with the plurality of the first orifices of the stationary component, wherein the displacement component is controlled to move toward the stationary component by the microprocessor so that the valve is in an open state.

7. The gas detecting device according to claim 6, wherein the displacement component is made of a charged material, and the stationary component is made of a bipolar conductive material, wherein the displacement component and the stationary component are controlled by the microprocessor to maintain in opposite polarity, and the displacement component moves toward the stationary component so that the valve is in the open state.

8. The gas detecting device according to claim 6, wherein the displacement component is made of a charged material, and the stationary component is made of a bipolar conductive material, wherein the displacement component and the stationary component are controlled by the microprocessor to maintain in the same polarity, and the displacement component moves toward the sealing component so that the valve is in a closed state.

9. The gas detecting device according to claim 6, wherein the displacement component is made of a magnetic material, and the stationary component is made of an electromagnet material whose magnetic polarity is changeable under control, wherein the displacement component and the stationary component are controlled by the microprocessor to maintain in opposite polarity, and the displacement component moves toward the stationary component so that the valve is in the open state.

10. The gas detecting device according to claim 6, wherein the displacement component is made of a magnetic material, and the stationary component is made of an electromagnet material whose magnetic polarity is changeable under control, wherein the displacement component and the stationary component are controlled by the microprocessor to maintain in the same polarity, and the displacement component moves toward the sealing component so that the valve is in a closed state.

11. The gas detecting device according to claim 1, wherein the sensor of the external sensor is at least one selected from the group consisting of an oxygen sensor, a carbon monoxide sensor, a carbon dioxide sensor and combinations thereof.

12. The gas detecting device according to claim 1, wherein the sensor of the external sensor is a volatile organic compound sensor.

13. The gas detecting device according to claim 1, wherein the sensor of the external sensor is at least one selected from the group consisting of a bacterial sensor, a virus sensor, a microorganism sensor and combinations thereof.

14. The gas detecting device according to claim 1, wherein the sensor of the external sensor is at least one selected from the group consisting of a temperature sensor, a humidity sensor and combinations thereof.

* * * * *